United States Patent [19]
Lee

[11] Patent Number: 5,395,340
[45] Date of Patent: Mar. 7, 1995

[54] INFUSION PUMP AND A METHOD FOR INFUSING PATIENTS USING SAME

[76] Inventor: Tzium-Shou Lee, 924 Maple Rd., Flossmoor, Ill. 60422

[21] Appl. No.: 31,524

[22] Filed: Mar. 15, 1993

[51] Int. Cl.⁶ ............................................. A61M 1/00
[52] U.S. Cl. ..................................... 604/151; 604/67; 128/DIG. 13
[58] Field of Search ............... 128/DIG. 12, DIG. 13; 604/65, 66, 67, 151, 246; 417/44

[56] References Cited

U.S. PATENT DOCUMENTS

| | | | |
|---|---|---|---|
| 3,590,809 | 7/1971 | London | 128/DIG. 13 |
| 3,655,123 | 4/1972 | Judson et al. | 604/67 |
| 4,898,578 | 2/1990 | Rubalcaba, Jr. | 604/66 |
| 4,943,279 | 7/1990 | Samiotes et al. | 604/154 |

*Primary Examiner*—C. Fred Rosenbaum
*Assistant Examiner*—Perry E. Van Over
*Attorney, Agent, or Firm*—Hill, Steadman & Simpson

[57] ABSTRACT

An improved infusion pump and a method for infusing patients using same. The infusion pump is modified to utilize a plurality of different drugs, each formulated at a mean effective dosage and toxicity level such that the infusion rate is the same for the drugs. More specifically, the control means of the infusion pump has a single drug label plate affixed to the pump and adjustable controls which are used in setting the mean effective dosage of the drug to be infused, the body weight of the patient to be infused, and the bolus or initial dosage of the drug to be infused. The method of the present invention comprises preparing the formulation of the plurality of different drugs, each at a mean effective dosage and, in combination with the infusion pump of the invention, infusing the drugs into patients at the same rate.

11 Claims, 1 Drawing Sheet

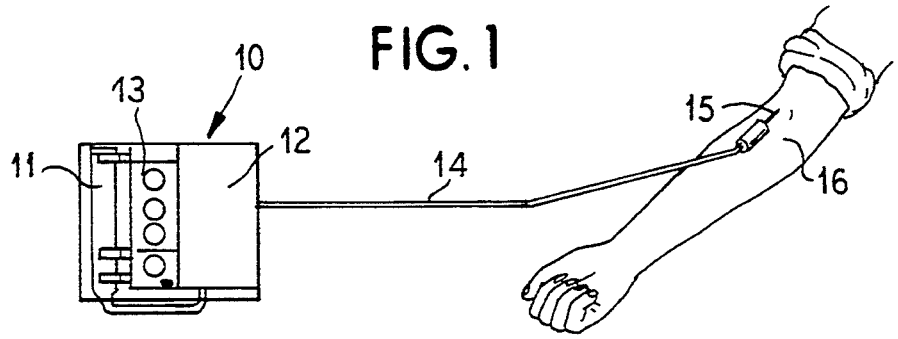
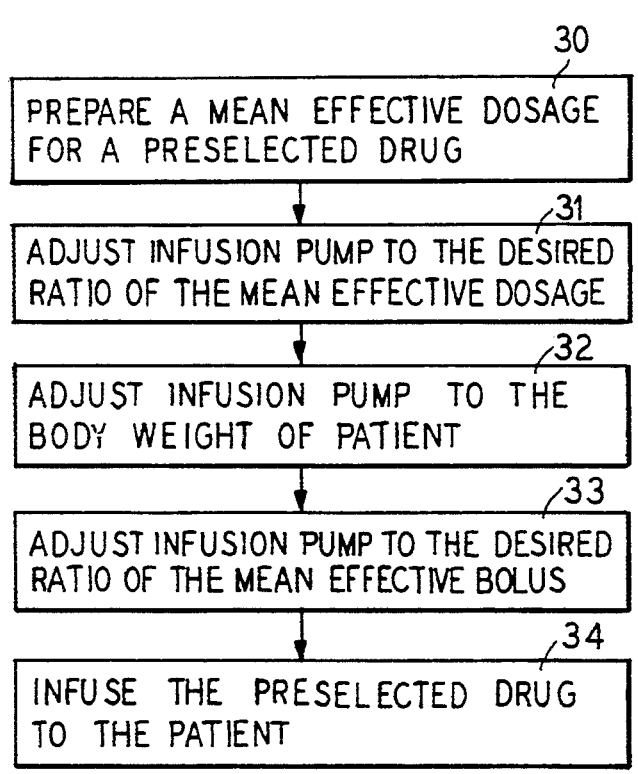
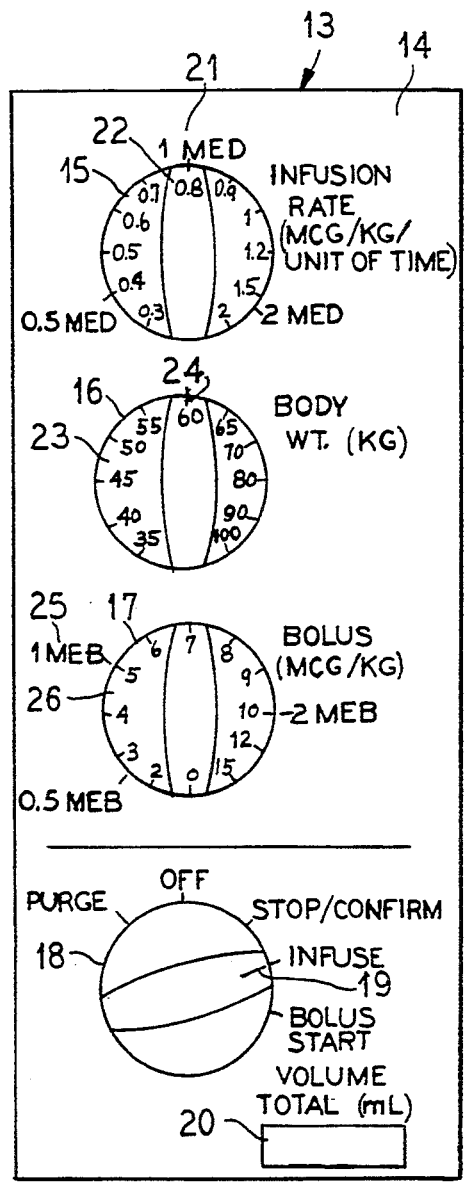

INFUSION PUMP AND A METHOD FOR INFUSING PATIENTS USING SAME

BACKGROUND OF THE INVENTION

The present invention relates to an improved infusion pump and a method for infusing patients using same.

During the course of medical treatment, drugs are necessarily administered to patients over a period of time (i.e., several minutes, hours, days). Rather than relying on the manual injection of bolus doses of drugs using syringes or on manually setting the drip rate of gravity-fed intravenous infusion sets, health professionals are utilizing infusion devices and systems that electronically or mechanically control the infusion rate of drugs as they are being administered to patients.

The most common application of infusion devices is for the maintenance of appropriate fluid levels in patients. Fluid therapy is commonly used in the treatment of burns, the pre- and postoperative management of surgical patients, and in the treatment of dehydration.

The administration of drugs provides the greatest challenge to infusion devices. For a drug to be effective, the concentration of any drug at its site of action must be sufficiently high for the drug to be effective, yet the concentration must not be too high for the drug to become toxic to the patient.

Widely used in differing applications such as delivering anesthetics during surgery, chemotherapy for cancer, and oxytocic agents for inducing labor, continuous drug infusion reduces the fluctuations in a drug's concentration that occurs with the more traditional modes of drug administration such as namely injections and pills. Moreover, continuous drug infusion assures a continuous therapeutic action as long as the infusion rate is appropriate.

Drug infusion systems consist of at least two components: 1) a mechanism that delivers the drug; and 2) a means of controlling the rate of delivery. A variety of devices are utilized by health care professionals for delivering drugs intravenously. An infusion pump is one such example.

Typically, with a powered infusion pump of the type similar to the Bard Infus O.R. ™ Pump (Bard MedSystems Division C.R. Bard, Inc., North Reading, Mass.), a predetermined volume of a drug is infused into a patient per unit of time as a function of the patient's body weight. The pump has a number of individual settable dials which include a dial for the infusion rate, the patient's body weight, and the bolus or initial dose of the drug being infused. For each drug that is delivered by an infusion pump to the patient, the bolus is typically calculated in micrograms per kilogram ("mcg/kg"). The infusion rate, also referred to as the maintenance dose, is calculated as micrograms per kilogram per minute ("mcg/kg/min"). The patient's body weight is generally calculated in kilograms ("kg").

Internally of a powered infusion pump, the settable dials have some relative setting position depending upon the degree of rotation of the external dial, and relate differently to each drug that is infused. As such, a different drug label plate is required for each drug when setting the external dials on the infusion pump.

With commercial infusion pumps like the Bard Infus O.R. ™ Pump, the difficulty occurs in that each drug has a different concentration and level of toxicity. The physician is, thus, required to first reference a drug card that is provided by the drug manufacturer in order to determine the appropriate induction bolus and continuous infusion rate for the drug.

As shown below, Table 1 represents a typical drug manufacturer's dosage reference card, which is a reproduction of a commercially produced dosage reference card of the general type provided to anesthesiologists to assist them in calculating the drug specific settings for the infusion pump. As shown for the drug DIPRIVAN ® (propofol), the bolus dosage ranges from 1.00 mg/kg to 2.75 mg/kg with a recommended dosage of 2.0–2.5 mg/kg for healthy young adults. The patient's weight is also factored into the bolus dosage. Thus, for a patient weighing 77 pounds (35 kg) and at a drug dosage of 2.00 mg/kg, the recommended bolus dosage is 7 mL. The infusion pump dial corresponding to the bolus dosage would then be set to deliver the 7 mL.

INDUCTION BOLUS

PATIENT WEIGHT — Pull slide to set indicator at patient weight.

| POUNDS | 66 | 77 | 88 | 99 | 110 | 121 | 132 | 143 | 154 | 165 | 176 | 187 | 198 | 209 | 220 | 231 | 242 | 253 | 264 |
|---|---|---|---|---|---|---|---|---|---|---|---|---|---|---|---|---|---|---|---|
| KILOGRAMS | 30 | 35 | 40 | 45 | 50 | 55 | 60 | 65 | 70 | 75 | 80 | 85 | 90 | 95 | 100 | 105 | 110 | 115 | 120 |

REPEAT BOLUS

If repeated bolus injections are used for maintenance of anesthesia, increments of 25% to 50% of the induction dose may be given. The patient's clinical response will determine the amount and frequency of incremental injections.

Read bolus dosage (mL) in window below.

| Dosage should be individualized. Healthy young adults are likely to require 2.0–2.5 mg/kg. Give in increments of approx 4 mL every 10 seconds. In the elderly, debilitated, hypovolemic, and/or ASA III or IV, reduce dosage by approx 50% (2 mL every 10 seconds). | | |
|---|---|---|
| 1.00 mg/kg | 3.5 | |
| 1.25 mg/kg | 4.4 | |
| 1.50 mg/kg | 5.3 | |
| 1.75 mg/kg | 6.1 | mL |
| 2.00 mg/kg | 7 | |
| 2.25 mg/kg | 7.9 | |
| 2.50 mg/kg | 8.8 | |
| 2.75 mg/kg | 9.6 | |

Each mL of DIPRIVAN contains 10 mg propofol.

A similar sequence of steps is followed by the physician when determining the appropriate continuous infusion rate for a drug. The infusion rate guidelines for DIPRIVAN ® are shown in Table 2 below. For example, the continuous infusion rate for a patient weighing 77 pounds (35 kg) at a desired dosage of 10 mg/kg/h is 35 mL/h. The infusion pump external dial corresponding to the infusion rate is, thus, set at the desired rate of 35 mL/h.

CONTINUOUS INFUSION

PATIENT WEIGHT — Pull slide to set indicator at patient weight.

| POUNDS | 66 | 77 | 88 | 99 | 110 | 121 | 132 | 143 | 154 | 165 | 176 | 187 | 198 | 209 | 220 | 231 | 242 | 253 | 264 |
|---|---|---|---|---|---|---|---|---|---|---|---|---|---|---|---|---|---|---|---|
| KILOGRAMS | 30 | 35 | 40 | 45 | 50 | 55 | 60 | 65 | 70 | 75 | 80 | 85 | 90 | 95 | 100 | 105 | 110 | 115 | 120 |

Read infusion rate (mL/h) for desired dosage in window below.

| | | |
|---|---|---|
| Variable-rate infusion should be titrated to the desired clinical effect, generally 6–12 mg/kg/h (0.1–0.2 mg/kg/min). | 3 mg/kg/h | 10.5 |
| | 6 mg/kg/h | 21 |
| | 7 mg/kg/h | 24.5 |
| | 8 mg/kg/h | 26 |
| | 9 mg/kg/h | 31.5 mL/h |
| | 10 mg/kg/h | 35 |
| | 11 mg/kg/h | 38.5 |
| | 12 mg/kg/h | 42 |
| | 15 mg/kg/h | 52.5 |

Each mL of DIPRIVAN contains 10 mg propofol.

Because of the vast number of drugs and the different concentrations at which each drug can be infused, physicians are inundated with numerous drug reference cards. Physicians tend to carry around the drug cards as a reference for setting the dials on the infusion pump, or alternatively, physicians commit to memory the various infusion guidelines for a limited group of drugs. A major disadvantage of the existing system is that errors occur when physicians attempt to memorize the various drug infusion guidelines. Further, the existing system encourages physicians to use the same group of drugs repeatedly to avoid learning new drug infusion guidelines. As a result, physicians are more likely to continue using the drugs and, thus, the drug infusion guidelines with which they are most familiar, rather than trying newly marketed drugs.

SUMMARY OF THE INVENTION

The present invention provides an improved infusion pump and a method for infusing drugs into patients using same. To this end, the present invention provides an infusion pump which utilizes a preselected drug from a plurality of different drugs, each formulated at a mean effective dosage and toxicity level such that the infusion rate for all drugs is the same. The mean effective dosage of a drug is calculated as a predetermined anesthesia value for individuals of an average body weight for administration over a given unit of time. The infusion pump's control means is modified to reflect the standardization of the mean effective dosage for a plurality of drugs. The modification is based on the use of a single drug label plate, which may be a permanent face portion of the pump, for selecting the infusion rate, body weight of the patient, and bolus or initial dosage of the drug to be infused. This feature provides an advantage over existing commercial infusion pumps, which require a different drug label plate for each drug that is infused.

The improved infusion pump and the method of the present invention eliminate the confusion and mistakes that are likely to occur when a physician attempts to memorize bolus and infusion dosages for a variety of drugs. Further, with the infusion pump of the present invention, physicians are more likely to try newly marketed drugs, since infusion guidelines for each drug will not have to be referred to and/or memorized.

In one embodiment of the present invention, the drug is an anesthetic.

In another embodiment, the control means comprises a single drug label plate affixed to the pump means, external dial members on said pump means for affecting the volumetric rate, and indicia means for indicating a relative position of each of the dial members relative to the single drug label plate.

In another embodiment, the indicia are located on the dial members.

In yet another embodiment, the indicia are located on the single drug label plate.

In a further embodiment, a multiple of the mean effective dosage is infused into a patient.

In another embodiment, a fraction of the mean effective dosage is infused into the patient.

BRIEF DESCRIPTION OF THE DRAWINGS

FIG. 1 is a diagrammatic view of an infusion pump assembly for delivering drugs to patients intravenously.

FIG. 2 is an enlarged view of the control means of the infusion pump assembly of the present invention for setting the volumetric delivery rate of the infusion pump, showing an adjustable dial member having setting indicia based on the mean effective dosage ("MED") of the drug to be infused, a second adjustable dial member having setting indicia based on the body weight of the patient to be infused, a third adjustable dial member having setting indicia based on the mean effective bolus ("MEB") or initial dosage of the drug to be infused, and a fourth adjustable dial member having setting indicia based on the operating mode of the infusion pump.

FIG. 3 is a flow sheet describing the overall process of preparing a mean effective dosage of a preselected drug, adjusting the infusion pump to the desired ratio of the mean effective dosage, the body weight of the patient, and the desired ratio of the mean effective bolus in accordance with the principles of the present invention, and then delivering the preselected drug to the patient.

DETAILED DESCRIPTION OF THE PRESENTLY PREFERRED EMBODIMENTS

The present invention provides a process for infusing drugs into patients, wherein a plurality of different drugs are each formulated at a mean effective dosage and toxicity level, such that each drug is infused into a patient at the same rate. For all drugs, the mean effective dosage is calculated as the predetermined anesthesia value for individuals of an average body weight (i.e., 70 kg) for administration over a given unit of time. It is contemplated that the various drug manufacturers will determine the MED for a preselected drug for infusion as well as the MEB dosage. The MEB or the initial startup dosage for a drug is calculated as the appropriate volume of the mean effective dosage that is required to decrease the patient's level of consciousness. It is further contemplated that a fraction or multiple of the MEB and/or the MED can be administered to the patient. With the process of the present invention, it is contemplated that any drug type can be used, most especially anesthetics.

For practicing the process, the present invention provides an improved infusion pump comprising: drug means comprising a plurality of different drugs, each formulated at a mean effective dosage for infusion at the same rate; a reservoir means for holding a selected one of said different drugs of said drug means; a pump means for transferring the one drug from the reservoir means through the pump means and into a patient; a control means for said pump means for controlling the volumetric rate of transferring the drug means from the pump means into the patient; and an intravenous delivery means for communicating the drug means from the pump means into the patient.

The infusion pump's control means is modified to reflect the process of preparing a number of different drugs, each formulated at a mean effective dosage for infusion at the same flow rate. Instead of an infusion pump having a different drug label plate for each drug as is currently used in the art, the present invention provides an infusion pump requiring only a single drug label plate, which reflects the standardization of the MED and MEB for a plurality of drugs. More specifically, the control means of the infusion pump comprises a single drug label plate affixed to the pump means, external dial members on said pump means for affecting the volumetric rate, and indicia means for indicating a relative position of each of the dial members relative to the drug label plate. A set of indicia indicates one position of one of the dial members at which the pump volumetric rate is equal to 1 MED and where other indicia indicate fractions or multiples thereof. Another set of indicia indicates one position of one of the dial members at which the bolus dosage is equal to 1 MEB and where other indicia indicate fractions or multiples thereof. Yet another set of indicia indicates one position of one of the dial members at which the body weight of the patient is shown in kilograms.

There is an internal control in the infusion pump which is computerized and receives the input from the control dial members, and in turn, modifies the driving rate of the pump.

By way of example, and not limitation, the following illustrations serve to further illustrate the present invention in its preferred embodiments.

FIG. 1 shows an infusion pump assembly 10 as typified by the Bard Infus O.R. TM Pump. The infusion assembly 10 comprises a reservoir 11 for holding a drug selected from a plurality of different drugs, each formulated at a mean effective dosage for infusion at the same rate, an internal pump 12 for transferring the selected drug from the reservoir 11 through the internal pump 12 and into a patient, a control means 13 for the internal pump 12 for controlling the volumetric rate of transferring the selected drug from the internal pump 12 into the patient; and an intravenous delivery means 14 having a needle 15 at one end for communicating the selected drug from the internal pump 12 into the arm 16 of the patient.

FIG. 2 shows control means 13 comprising a single drug label plate 14 which is affixed to the internal pump 12, a series of external dial members 15-18 on the internal pump 12 for affecting the volumetric rate, and indicia means comprising a plurality of different setting indicators 19-26 for indicating a relative position of each of the dial members 15-18 relative to the single drug label plate 14. Dial member 15 controls the desired infusion rate of the preselected drug. Dial member 16 controls the body weight of the patent to be infused. Dial member 17 controls the bolus dosage to be delivered to the patient. Dial member 18 controls the switch mode of the infusion pump assembly 10. For example, indicator point 19 on dial member 18 is set to the "infuse" position. A readout indicator 20 indicates the total volume in milliliters (mL) of the drug being infused.

As further shown in FIG. 2, indicator 21 indicates 1 MED or the mean effective dosage of the drug being infused, and numerical scale indicator 22, which when aligned with indicator 21, indicates the actual dosage in mcg/kg/unit of time of 1 MED. For the example shown in FIG. 2, 1 MED is 0.8 mcg. However, the numerical value for 1 MED for a drug may vary, since it is based upon a predetermined anesthesia value for individuals of a predetermined average body weight. Numerical scale indicator 23 indicates a body weight range in kilograms (kg) of the patient. When numerical scale indicator 23 is aligned with indicator 24, the body weight of the patient is indicated, in this example, 60 kg.

Indicator 25 indicates 1 MEB or the mean effective bolus dosage that is delivered to the patient. Numerical scale indicator 26, which when aligned with indicator 25, indicates the actual bolus dosage in mcg/kg that is equivalent to 1 MEB. Although the example in FIG. 2 shows 1 MEB equal to 5 mcg, the value of 1 MEB, too, varies depending on the drug selected. It should also be noted that multiples or fractions of 1 MED and 1 MEB, for example 0.5 MED/2 MED and 0.5 MEB/2 MEB, are indicated on the control means 13 shown in FIG. 2.

FIG. 3 shows a series of process steps that are practiced in carrying out the principles of the present invention. According to process step 30, a plurality of different drugs are prepared, each formulated at a mean effective dosage for infusion at the same rate. With this process, each drug is prepared at a certain toxicity and dosage level so that the MED is delivered to the patient at a single flow rate (i.e., 5 cc/hour). The process steps 31-34 of the present invention are practiced with an infusion pump having adjustable controls for setting the volumetric delivery rate of the pump with one control having setting indicia based on the MED, a second control having setting indicia based on the body weight of the patient receiving the drug, and a third control having setting indicia based on the MEB. If, in the opinion of the treating physician, a multiple or fraction of 1 MED and/or 1 MEB is more appropriate given the patient's clinical history, then the controls are adjusted accordingly, for example, 0.5 MED and 2 MEB.

Once process steps 30-33 are conducted, the appropriate control is adjusted to the desired pump mode (i.e., purge, off, stop/confirm, infuse, bolus start), which allows delivery of the preselected drug intravenously to the patient.

The improved infusion pump and the method of delivering drugs intravenously to patients using the infusion pump eliminate the need for different drug label plates with the use of each drug, and the complex calculations for determining volumetric rates for infusion.

The Bard Infus O.R. ™ Pump is used herein for the purpose of describing the improved infusion pump of the present invention. However, it is contemplated that other commercially manufactured infusion pumps could be similarly modified to practice the present invention.

It should be understood that various changes and modifications to the presently preferred embodiments described herein will be apparent to those skilled in the art. Such changes and modifications can be made without departing from the spirit and scope of the present invention, and without diminishing its attendant advantages. It is therefore intended that such changes and modifications be covered by the appended claims.

I claim:

1. An infusion pump for the infusion of drugs into patients, comprising:
    drug means comprising a plurality of different drugs, each formulated at a mean effective dosage for infusion at the same rate;
    a reservoir means for holding a selected one of said different drugs of said drug means;
    a pump means for transferring the one drug from the reservoir means through the pump means and into a patient;
    a control means for said pump means for controlling the volumetric rate of transferring the drug means from the pump means into the patient, said control means comprising a single drug label affixed to said pump means, external dial members on the pump means for affecting the volumetric rate, and indicia means for indicating a relative position of each of the dial members relative to the single drug label plate, and said indicia means including indicia indicating one position of one of the dial members at which the pump volumetric rate is equal to one mean effective dosage and other indicia indicating multiples or fractions thereof; and
    an intravenous delivery means for communicating the drug means from the pump means into the patient.

2. The infusion pump of claim 1, wherein the drug means is an anesthetic.

3. The infusion pump of claim 1, wherein the indicia means are located on the dial members.

4. The infusion pump of claim 1, wherein the indicia means are located on the single drug label plate.

5. The infusion pump of claim 1, wherein the indicia means indicates the position of one of the dial members at which the body weight of the patient is indicated.

6. The infusion pump of claim 1, wherein the indicia means indicates one position of one of the dial members at which the bolus dosage is equal to one mean effective bolus and where other indicia indicate multiples or fractions thereof.

7. A method for infusing drugs into a patient, comprising the steps of:
    a) preparing a plurality of different drugs, each formulated at a mean effective dosage for infusion at the same rate;
    b) providing an infusion pump having adjustable controls for setting the volumetric delivery rate of the pump with one control having setting indicia based on mean effective dosage, a second control having setting indicia based on patient body weight, and a third control having setting indicia based on mean effective bolus;
    c) adjusting the adjustable control to the desired ratio of the mean effective dosage;
    d) adjusting the second control to indicate the body weight of the patient;
    e) adjusting the third control to indicate the desired ratio of the mean effective bolus; and
    f) infusing the drug into the patient.

8. The method of claim 7, wherein a multiple of the mean effective dosage is infused into the patient.

9. The method of claim 7, wherein a fraction of the mean effective dosage is infused into the patient.

10. The method of claim 7, wherein a multiple of the mean effective bolus is infused into the patient.

11. The method of claim 7, wherein a fraction of the mean effective bolus is infused into the patient.

* * * * *